US00PP33267P2

(12) United States Plant Patent
Hansen

(10) Patent No.: US PP33,267 P2
(45) Date of Patent: Jul. 13, 2021

(54) *HOSTA* PLANT NAMED 'TIME IN A BOTTLE'

(50) Latin Name: ***Hosta* hybrid (Tratt.)**
Varietal Denomination: Time in a Bottle

(71) Applicant: Hans A Hansen, Zeeland, MI (US)

(72) Inventor: Hans A Hansen, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 0 days.

(21) Appl. No.: 16/974,100

(22) Filed: Sep. 30, 2020

(51) Int. Cl.
*A01H 5/12* (2018.01)
*A01H 6/12* (2018.01)

(52) U.S. Cl.
USPC ..... Plt./353

(58) Field of Classification Search
USPC ..... Plt./353
See application file for complete search history.

*Primary Examiner* — Susan McCormick Ewoldt

(57) ABSTRACT

A new and distinct *Hosta* plant named 'Time in a Bottle' of arching, lanceolate, chartreuse leaves having a lustrous underside and moderately wavy margins. The flowers are dark purple and tightly congested on upright to slightly-outwardly dark-reddish scapes above the foliage and typically do not open. 'Time in a Bottle' has excellent, small, compact, mounded habit and is useful in the landscape, in containers, as a specimen or en masse.

3 Drawing Sheets

Botanical classification: *Hosta* hybrid (Tratt.).
Variety denomination: 'Time in a Bottle'.

STATEMENT REGARDING PRIOR DISCLOSURES UNDER 37 CFR 1.77(B)(6)

*Hosta* 'Time in a Bottle' was first introduced by the inventor as a non-enabling description and photographs through the International Cultivar Registration Authority registration in late 2019. No plants of *Hosta* 'Time in a Bottle' have been sold, in this country or anywhere in the world, nor has any disclosure of the new plant been made, more than one year prior the filing date of this application.

BACKGROUND AND ORIGIN OF THE PLANT

The present invention relates to a new and distinct *Hosta* plant, *Hosta* 'Time in a Bottle' hereinafter also referred to as the new plant or by the cultivar name, 'Time in a Bottle'. *Hosta* 'Time in a Bottle' was a cross by the inventor between two non-patented, unreleased, proprietary hybrids on Aug. 23, 2013 at a wholesale perennial nursery in Zeeland, Mich., USA. The female parent was 'Atom Smasher' (not patented) and the male parent was identified as 11-463-02 (not patented). The new plant was assigned the breeder code 13-443-x and passed the initial evaluation in the summer of 2015. It has been asexually propagated by division at the same nursery since 2018 and also by careful shoot tip plant tissue culture with the resultant asexually propagated plants having retained all the same traits as the original plant. *Hosta* 'Time in a Bottle' is stable and reproduces true to type in successive generations of asexual reproduction.

There are over 7,000 registered and unregistered *Hostas* with The American *Hosta* Society, which is the International Cultivar Registration Authority for the genus *Hosta*. Several of these have chartreuse leaf blades with wavy margins. The most similar *Hosta* cultivars known to the applicant are 'Party Streamers' copending U.S. Plant patent application Ser. No. 16/974,299, 'Silly String' U.S. Plant Pat. No. 32,127, 'Lemon Lime' (not patented), 'Chartreuse Wiggles' (not patented), 'Bitsy Gold' (not patented), 'Purple Lady Fingers' (not patented) and 'Curly Fries' (not patented).

'Silly String' has blue-green foliage, is smaller in habit and foliage size, and the flower opens broadly. 'Lemon Lime' has smaller habit, shorter leaves and the flowers open much wider. 'Bitsy Gold' has narrower and smaller leaves without any ruffling, and the flowers open broadly. 'Purple Lady Fingers' has wider green foliage with a larger habit but the flowers do not open when mature. 'Curly Fries' has longer narrower leaves that are more ruffled and the flowers open when mature. 'Party Streamers' has a slightly larger habit with slightly larger leaves that are more arching, and the flowers open to display strong violet color with darker veins. 'Chartreuse Wiggles' has smaller habit with smaller and narrower foliage and the flowers are campanulate.

The female parent is smaller in habit with smaller and narrower foliage that is more yellowish hue and the margin is more wavy and rippled. The male parent has broader foliage with more ruffles and forms a larger clump. Both parents have yellow to chartreuse-colored foliage.

Other *Hosta* cultivars may have traits similar to 'Time in a Bottle' but the new plant differs from the above listed cultivars and all other *Hostas* known to the applicant, by the combination of the following traits.

1. Leaves are small-sized, lanceolate, with narrowly acute apices and attenuate base;
2. Arching chartreuse leaves have a moderately wavy margin;
3. Underside of leaf lustrous;
4. Compact mounded habit and useful in the garden as edging or front border, in containers, as a specimen or en masse;
5. Flowers are dark-purple, closely-arranged, on dark reddish scapes and the tepals typically do not open;

BRIEF DESCRIPTION OF THE DRAWING

The photograph of the new plant demonstrates the overall appearance of the plant, including the unique traits. The colors are as accurate as reasonably possible with color reproductions. Ambient light spectrum, temperature, source and direction may cause the appearance of minor variation in color.

The drawings shows the new plant in a trial garden at a nursery in Zeeland, Mich. with supplement fertilizer and water as needed.

DETAILED BOTANICAL DESCRIPTION

Figure 1:
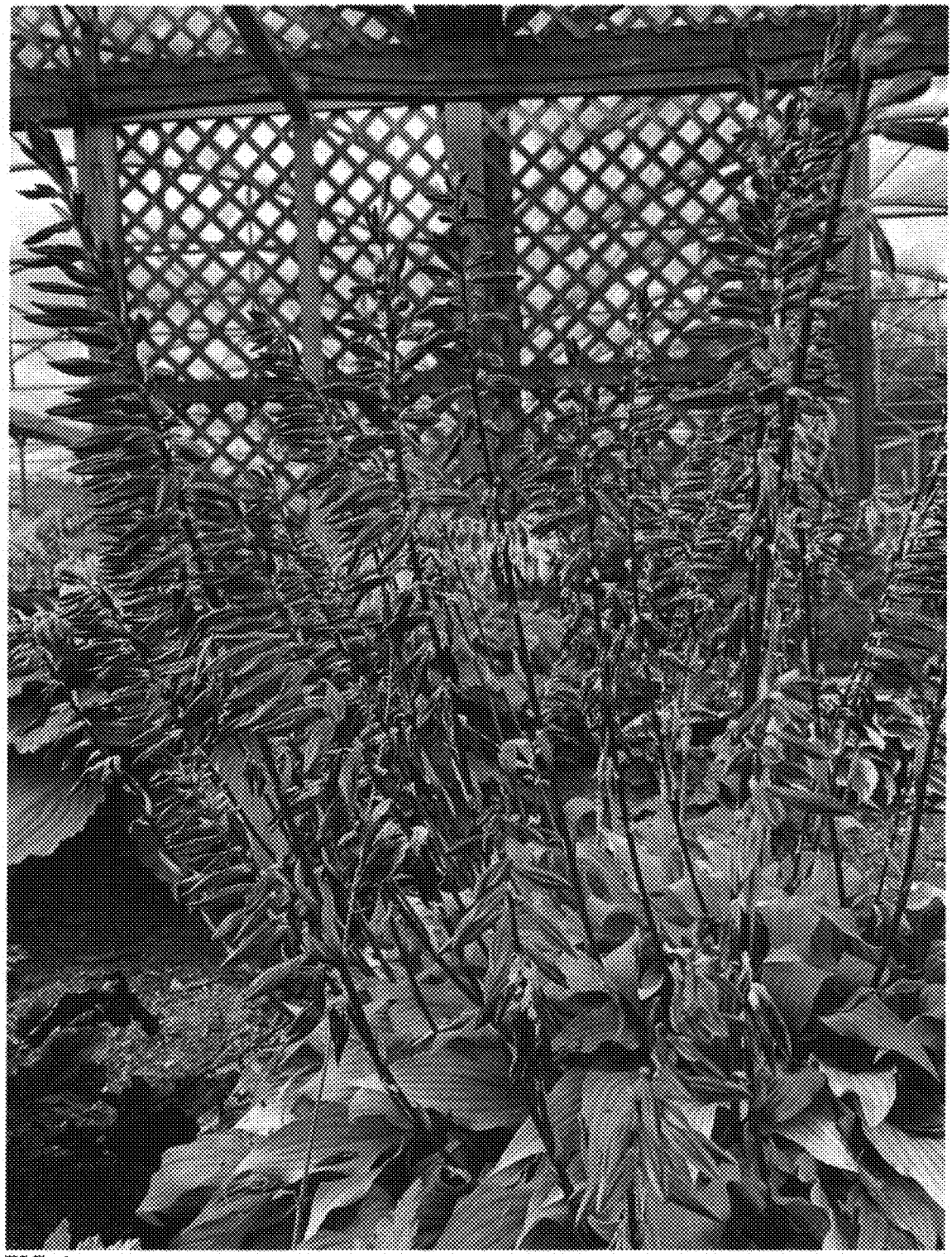
FIG. 1 shows the landscape habit of a six-year-old plant just before flowering.
Figure 2:
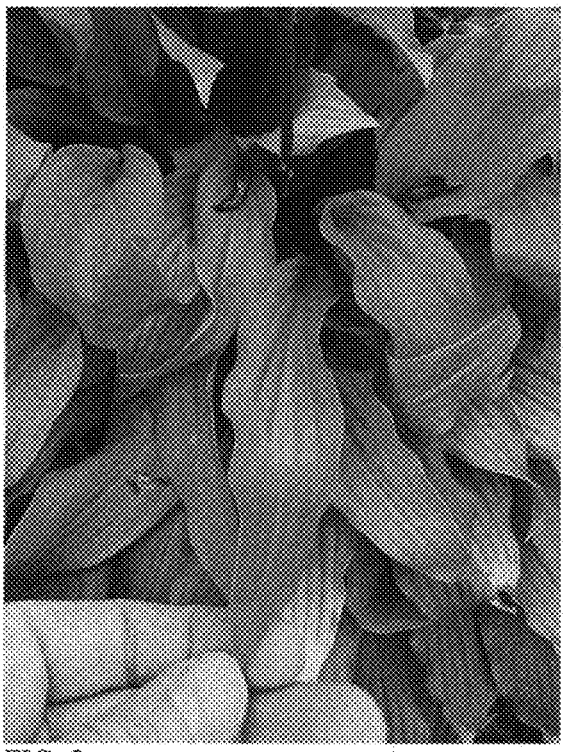
FIG. 2 shows a close-up of the flowers and buds on a six-year-old plant.
Figure 3:
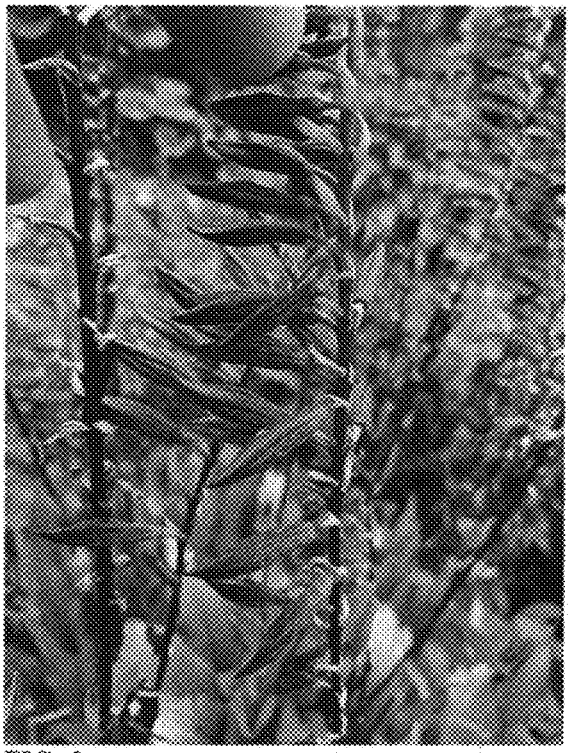
FIG. 3 shows a close-up of the foliage of a six-year-old plant.
Figure 4:
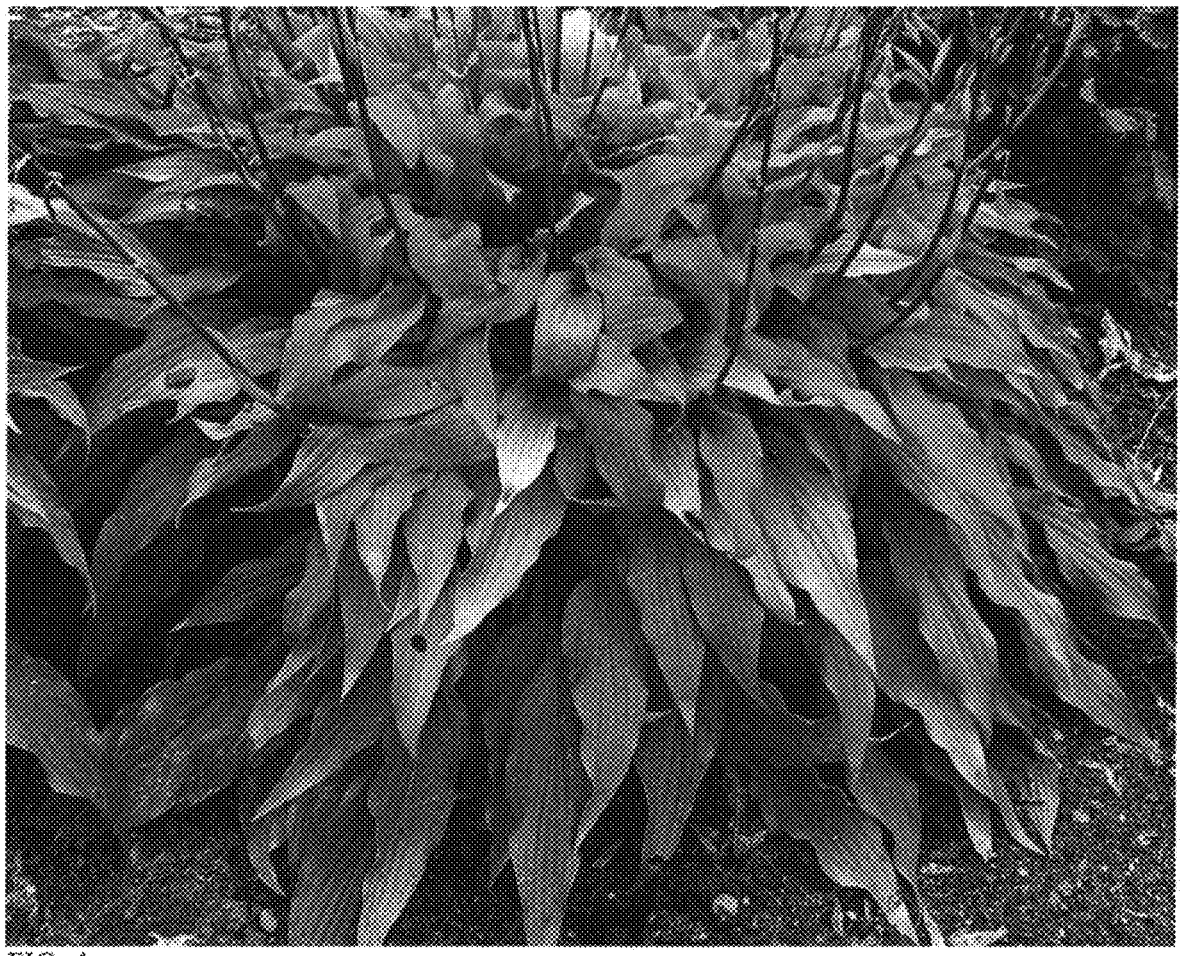
FIG. 4 shows the foliage landscape habit of a six-year-old plant.

The following descriptions and color references are based on the 2015 edition of The Royal Horticultural Society Colour Chart except where common dictionary terms are used. The new plant, *Hosta* 'Time in a Bottle', has not been observed under all possible environments. Those skilled in the art will appreciate that certain characteristics will vary with plants that are more mature or plants that are less mature. The phenotype may vary slightly with different environmental conditions, such as temperature, light, fertility, moisture and maturity levels, but without any change in the genotype. The following observations and size descriptions are of a six year old plant in a shaded trial garden in Zeeland, Mich. with supplemental water and fertilizer:

Botanical classification: *Hosta* x hybrid;

Parentage: Female or seed parent 'Atom Smasher'; male or pollen parent is the proprietary hybrid 11-463-02 which is a hybrid of 'Curly Fries' (not patented);

Propagation: Garden division and sterile shoot tip plant tissue culture;

Time to initiate roots from tissue culture: About two to three weeks;

Growth rate: Moderately vigorous;

Crop time: About three months to four months to finish during the spring in a one-liter container from rooted tissue culture plantlet;

Rooting habit: Fleshy, lightly branching;

Root color: Nearest RHS NN155C when actively growing;

Plant shape and habit: Hardy herbaceous perennial with basal rosette of leaves emerging from rhizomes producing a short, compact, mound of arching petioles and leaves and upwardly scapes flowering above foliage;

Plant size: Foliage height about 30.5 cm above soil line to the top of the leaves, about 61.0 cm tall to the top of the flowers and about 91.0 cm wide at the widest point at the soil line;

Foliage description: Glabrous and dull adaxial and glabrous and slightly lustrous abaxial; lanceolate; narrowly acute apex, attenuate base; margin entire, moderately sinuate; flexible; smooth, without blistering, dimpling or bulging;

Leaf blade size: To about 17.8 cm long and 5.5 cm wide; average about 15.0 cm long and 4.5 cm wide;

Leaf blade color: Young adaxial between RHS 150B and RHS 150C, abaxial between RHS 150B and RHS 150C; mid-season and later adaxial variable nearest RHS 137C and between RHS 146D and RHS 151D, mid-season and later abaxial between RHS 146D and RHS 151D;

Petiole: Glabrous and slightly lustrous both adaxial and abaxial; concavo-convex proximally and distally; flexible; to 19.5 cm long, 8.0 mm wide at base and 4.0 mm deep; average about 17.0 cm long and 7.0 mm wide;

Petiole color: Young adaxial and abaxial basal one-third between RHS 150C and RHS 150B heavily maculate with N79C, distally between RHS 151D and RHS 146D; mature adaxial nearest RHS 146D and maculate more concentrated to solid proximally and less concentrated distally with nearest RHS 187D, mature abaxial distally nearest RHS 146B, proximal three-quarters moderately maculate with nearest RHS 187D and center midrib nearest RHS 155A;

Veins: Typically five pairs and midrib; parallel; slightly costate and smooth on abaxial side;

Veins color: Adaxial nearest and between RHS 146D and RHS 151D, abaxial between RHS 146D and RHS 151D;

Flower description:

Buds one to two days prior to opening: Cycloidal with acute apex and truncate base; about 30.0 mm long and 9.0 mm in diameter at widest near center, with short narrowed tube at base about 3.0 mm long and 4.0 mm diameter;

Bud color: Blend between RHS 85A and RHS 86D with tepal margins nearest RHS 86A;

Flowers: Typically not opening; cycloidal; outwardly; to 30.0 mm long and 9.0 mm across; corolla fused in basal 18.0 mm, free in the distal 12.0 mm, (distal flowers smaller);

Inflorescence: Flowers tightly arranged in verticil near middle and individually separated above and below; flowering in distal 30.0 cm and about 5.5 cm across;

Flowering period: Scapes remain effective with flowers beginning mid-August for about four weeks; with about 44 flowers per scape; distinctly secund; no detectable fragrance;

Tepal: Two nearly identical sets of three, glabrous; lanceolate; entire margins; narrowly acute apices and fused in the basal 18.0 mm;

*Inner set*.—Approximately 30.0 mm long and 5.0 mm wide slightly above fusion point.

*Inner set color*.—Adaxial nearest RHS 79C; abaxial margins nearest RHS 86A, central portion including tube nearest RHS 86D.

*Outer set*.—Approximately 30.0 mm long and 9.0 mm wide slightly at fusion point.

*Outer set color*.—Adaxial nearest RHS 79C; abaxial margins nearest RHS 86A, central portion including tube nearest RHS 86D.

Gynoecium: One to six per flower; to 19.0 mm long; superior;

*Style*.—Cylindrical; twisted near base and distortedly bent; variable; about 9.0 mm long, 0.5 mm diameter; color nearest RHS 145D.

*Stigma*.—Puberulent; rounded; variable; about 0.5 mm across and 0.5 mm tall; color nearest RHS NN155A.

*Ovary*.—Ovoidal; superior; apex truncate; base truncate; to about 4.0 mm long and 3.5 mm diameter in middle; color apex and base nearest RHS N79A, with longitudinal lines of nearest RHS 145B.

Androecium: Not observed or rudimentary;

*Filaments*.—Two or fewer if present; to approximately 7.0 mm long and 0.2 mm in diameter; color nearest RHS 145D.

*Anthers*.—Not observed.

*Pollen*.—Not observed.

Flower fragrance: None observed;

Peduncle: Cylindrical; glabrous; slightly lustrous; usually one per mature division; about 35 per plant; semi-lustrous, glabrous; nearly vertical to slightly outwardly; to about 61.0 cm tall, and about 5.0 mm in diameter at base, average about 56 cm tall and 4.5 mm diameter at base;

Peduncle color: Proximal portion densely maculate nearest RHS 187C and basal portion less densely maculate nearest RHS 187C, with undertone of nearest RHS 145C;

Pedicel: Cylindrical; glabrous; glaucous; about 10.0 mm long and 1.5 mm diameter; outwardly to slightly upwardly;

Pedicel color: Variable; beginning nearest RHS N82D, maturing to a variable mix of nearest RHS196D and nearest RHS N81D;

Floral bracts: Each flower normally subtended by a single bract; lanceolate; narrowly acute apex and truncate base; entire margin; glabrous and matte abaxial and adaxial; to about 16.0 cm long 7.0 mm wide; decreasing in size distally; drying and dehiscing before flowers open;

Bract color: Variable; adaxial with portions of nearest RHS 146D, RHS 194C and blend between RHS 72A and RHS 72B with translucent margins about 0.5 mm wide; abaxial variable portions of nearest RHS 146D, RHS 147C and blend between RHS 72A and RHS 72B with translucent margins about 0.5 mm wide.

Fruit and seed: Not observed;

Disease resistance: The thick glaucous leaves provide some resistance to slug feeding. Other resistance to pests (including: *Odocoileus virginianus* and *Oryctotagus cuniculus*) and diseases common to *Hostas* is equal that typical of other cultivars. The plant grows best and shows best coloration with plenty of moisture, adequate drainage and light shade, but is able to tolerate some drought when mature. Hardiness at least from USDA zone 3 through 8, and other disease resistance is typical of that of other *Hostas*.

It is claimed:

1. A new and distinct *Hosta* plant cultivar named *Hosta* 'Time in a Bottle' as herein described and illustrated.

* * * * *